United States Patent
Popescu et al.

(10) Patent No.: US 8,928,887 B2
(45) Date of Patent: Jan. 6, 2015

(54) CHARACTERISTIC PARAMETERS OF CELLS AND TISSUE FROM QUANTITATIVE PHASE IMAGING

(71) Applicant: The Board of Trustees of the University of Illinois, Urbana, IL (US)

(72) Inventors: Gabriel Popescu, Champaign, IL (US); Huafeng Ding, Henrico, VA (US); Zhuo Wang, Beverly, MA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 125 days.

(21) Appl. No.: 13/775,788

(22) Filed: Feb. 25, 2013

(65) Prior Publication Data

US 2013/0236923 A1    Sep. 12, 2013

Related U.S. Application Data

(60) Provisional application No. 61/606,149, filed on Mar. 2, 2012.

(51) Int. Cl.
| | |
|---|---|
| *G01B 9/02* | (2006.01) |
| *G01N 21/47* | (2006.01) |
| *G01N 15/14* | (2006.01) |
| *G02B 21/00* | (2006.01) |
| *G01N 15/10* | (2006.01) |
| *G02B 21/18* | (2006.01) |

(52) U.S. Cl.
CPC ............ *G01N 21/47* (2013.01); *G01N 15/1434* (2013.01); *G01N 2015/1454* (2013.01); *G02B 21/0004* (2013.01); *G01N 2015/1006* (2013.01); *G01N 2015/1445* (2013.01); *G02B 21/18* (2013.01)
USPC ........................................... 356/450; 356/456

(58) Field of Classification Search
USPC ......... 356/450, 451, 453, 456, 458, 496, 503, 356/491
See application file for complete search history.

(56) References Cited

U.S. PATENT DOCUMENTS 8,184,298 B2    5/2012    Popescu et al. ............... 356/450

OTHER PUBLICATIONS

Ding et al., "Fourier Transform Light Scattering of Inhomogeneous and Dynamic Structures," *Phy. Rev. Lett.*, vol. 101, No. 23, pp. 238102-1-238102-4 (Dec. 2008).
Ding et al., "Optical properties of tissues quantified by Fourier-transform light scattering," *Opt. Lett.*, vol. 34, No. 9, pp. 1372-1374 (May 2009).
Wang et al., "Quantitative phase imaging with broadband fields," *Appl. Phys. Lett.*, vol. 96, No. 5, pp. 051117-1-051117-3 (Feb. 2010).
Wang et al., "Spatial light interference microscopy (SLIM)," *Opt. Exp.*, vol. 19, No. 2, pp. 1016-1026 (Jan. 2011).
Wang et al., "Scattering-phase theorem," *Opt. Lett.*, vol. 36, No. 7, pp. 1215-1217 (Apr. 2011).
Wang et al., "Tissue refractive index as marker of disease," *J. Biomed. Opt.*, vol. 16, No. 11, pp. 116017-1-116017-7 (Nov. 2011).

*Primary Examiner* — Tri T Ton
(74) *Attorney, Agent, or Firm* — Sunstein Kann Murphy & Timbers LLP

(57) ABSTRACT

Methods mapping a characteristic parameter of a specimen, such as a scattering mean free path and a scattering anisotropy factor, based on a quantitative phase shift measurement. The methods have steps of using spatial light interference microscopy (SLIM) to determine a quantitative phase shift as a function of position in a sample, and applying a generalized scatter-phase transformation to derive at least one of a scattering mean free path (MFP), a scattering anisotropy factor, and a thickness-independent parameter as a function of position in the sample. In some cases, the sample may be a slice of tissue or a cell.

6 Claims, 12 Drawing Sheets
(7 of 12 Drawing Sheet(s) Filed in Color)

*FIG. 4A*          *FIG. 4B*
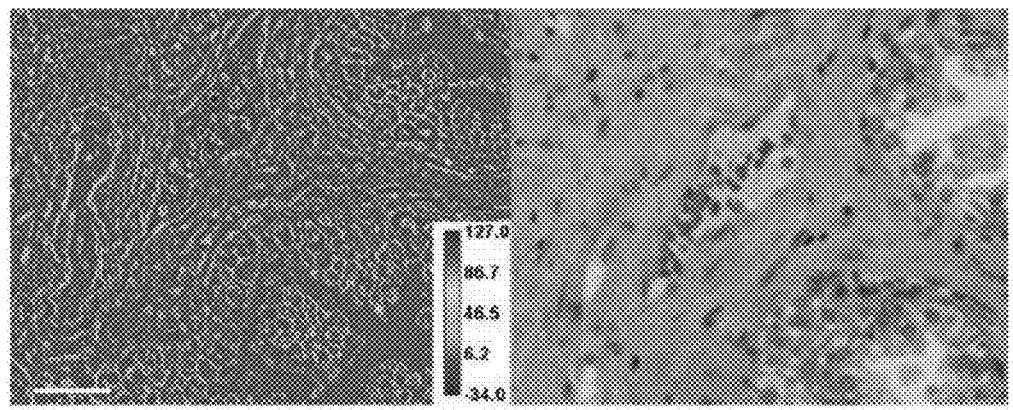
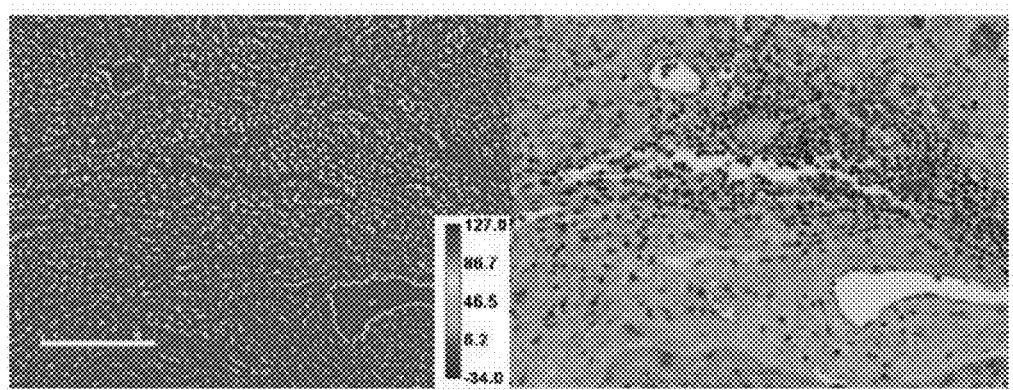
*FIG. 4C*          *FIG. 4D*

FIG. 4E  FIG. 4F

FIG. 5A
FIG. 5B
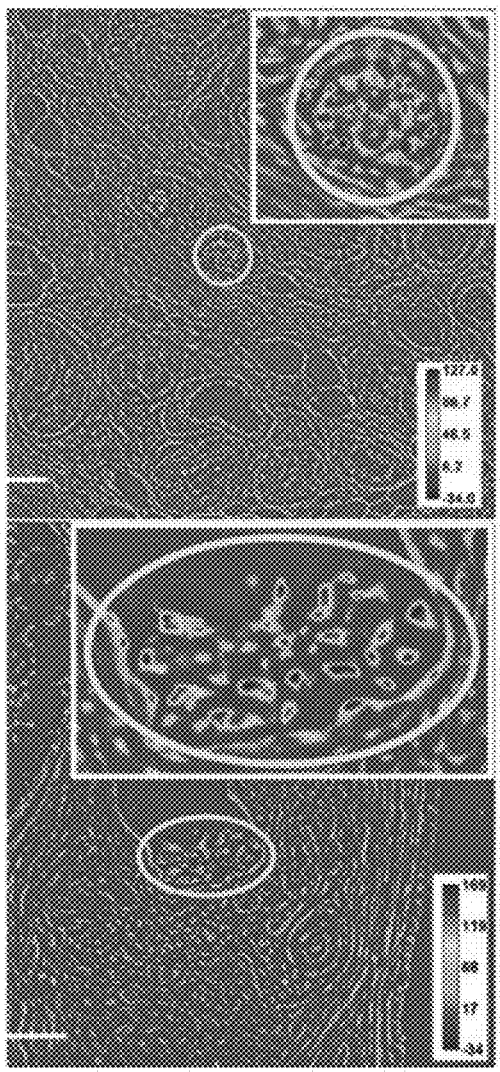
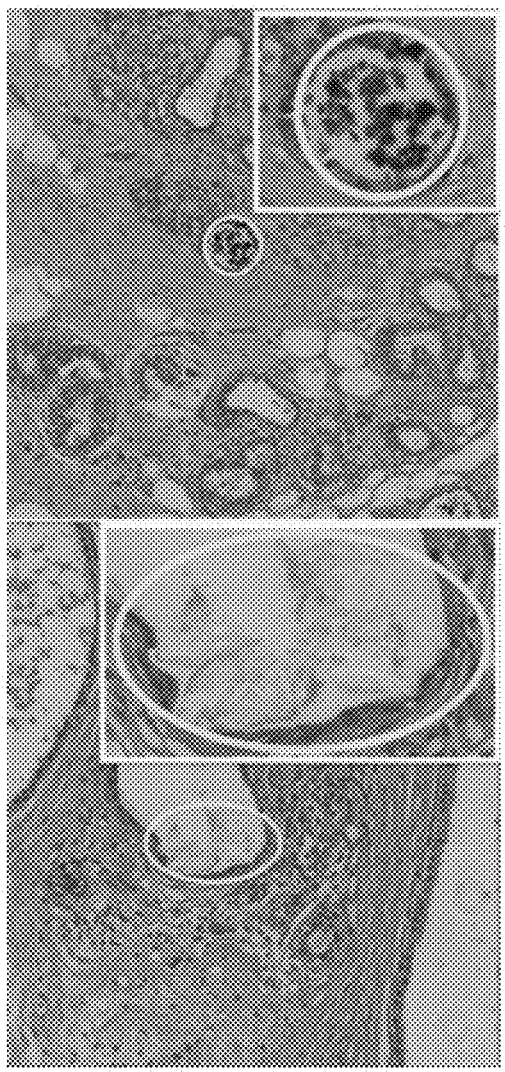
FIG. 5C
FIG. 5D

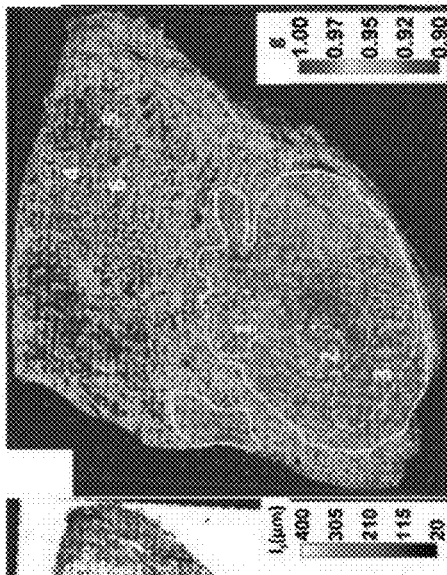
FIG. 6A
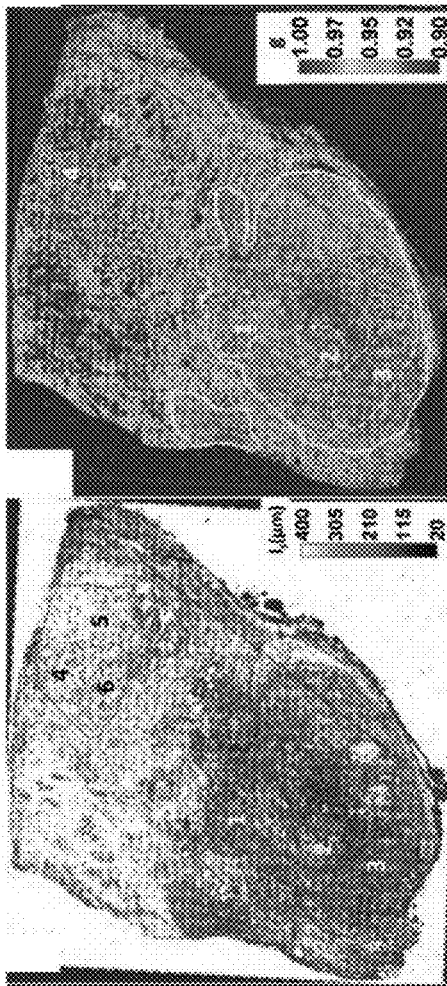
FIG. 6B
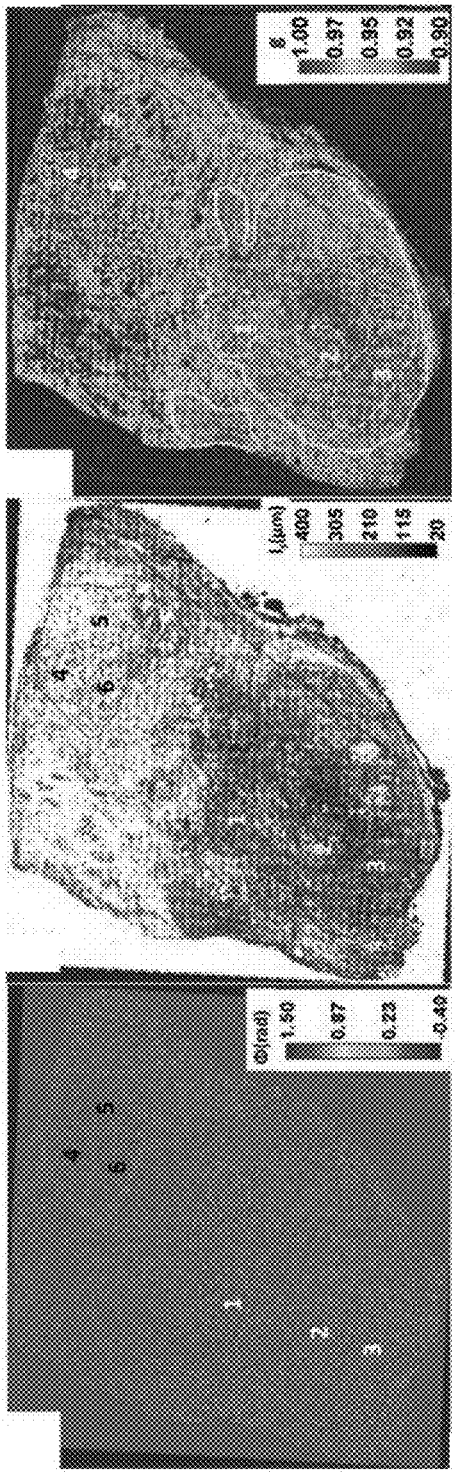
FIG. 6C
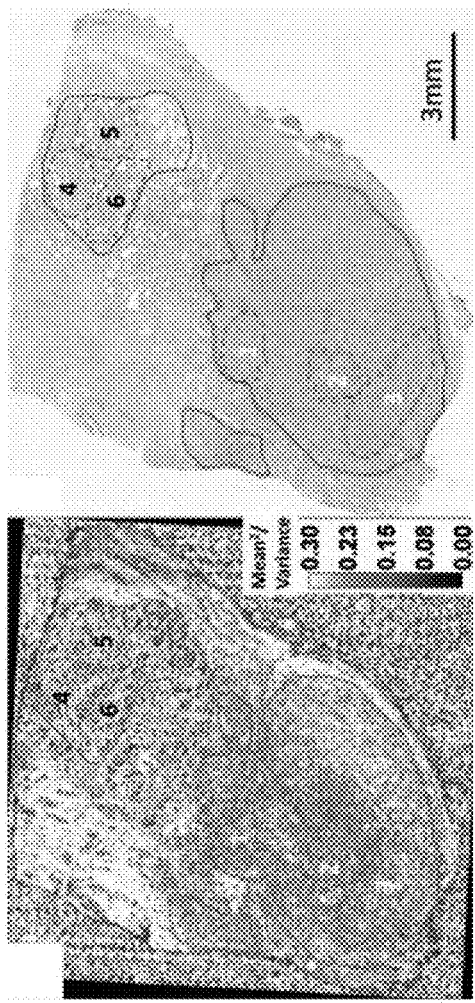
FIG. 6D
FIG. 6E ID# CHARACTERISTIC PARAMETERS OF CELLS AND TISSUE FROM QUANTITATIVE PHASE IMAGING This application claims priority from U.S. Provisional Patent Application Ser. No. 61/606,149, filed Mar. 2, 2012, and incorporated herein by reference.

This invention was made with government support under Grants CBET 08-46660 Career, and CBET 1040462 MRI, awarded by the National Science Foundation, and R21 CA147967-01, awarded by the National Cancer Institute. The Government has certain rights in the invention.

TECHNICAL FIELD

The present invention relates to methods for applying quantitative phase imaging to the derivation of a variety of characteristic parameter (including scattering parameters) of tissues and cells, and thereby also to the identification of cell pathologies.

BACKGROUND ART

Light scattering from tissues and cells has attracted extensive research interest, especially due to the potential it offers for in-vivo diagnosis. The starting point in light-scattering-based diagnosis is that normal and diseased tissues are characterized by scattering parameters that are measurably different. Translating such methods to the clinic requires knowledge of the optical properties associated with both healthy and diseased tissues. However, the direct measurement of these scattering parameters, which may include, but are not limited to, the scattering mean free path (MFP) $l_s$ and anisotropy factor g, is extremely challenging.

In the absence of absorption, the scattering mean free path, $l_s$, is the average distance between two adjacent scattering events or the distance over which the unscattered light decreases to 1/e of its original power. The parameter $l_s$, provides the characteristic length scale of the scattering process.

The anisotropy factor g is the average cosine of the scattering angle, g=<cos θ>, and is used to obtain the transport mean free path, $l_t=l_s/(1-g)$, which normalizes $l_s$ to larger values to account for forward-biased scattering (i.e., g>0).

The transport mean free path $l_t$ is a new quantity, which approaches $l_s$ as the individual scattering becomes isotropic (g→0). The physical meaning of $l_t$ (and its asymptotic limit, $l_s$) is the distance after which the direction of propagation is randomized.

The direct measurement of the foregoing scattering parameters is extremely challenging and, therefore, simulations, such as Monte Carlo, or finite-difference time-domain simulations, are often used iteratively instead.

Recently, Fourier transform light scattering (FTLS), the spatial analog of Fourier transform spectroscopy, was developed to provide angular scattering information from phase-sensitive measurements. FTLS is described in Ding et al., *Fourier Transform Light Scattering of Inhomogeneous and Dynamic Structures*, Phys. Rev. Lett., vol. 101, 238102 (2008), which is incorporated herein by reference. FTLS has been used to measure $l_s$ from angular scattering of tissue slices, and the anisotropy parameter g has been determined by fitting the scattering pattern with a Gegenbauer Kernel phase function, as reported by Ding, et al., *Optical properties of tissues quantified by Fourier-transform light scattering*, Opt. Lett., vol. 34, pp. 1372-74 (2009), hereinafter Ding (2009), incorporated herein by reference.

Measurement of scattering parameters may serve to characterize tissue, and, in particular, the presence and nature of tumorous tissue. In particular, breast cancer and prostate cancer are two of the most widespread cancers in the western world, accounting for approximately 30% of all cases. Following abnormal screening results, a biopsy is performed to establish the existence of cancer and, if present, its grade. The pathologist's assessment of the histological slices represents the definitive diagnosis procedure in cancer pathology and guides initial therapy.

It is thus of great value to place new quantitative methods at the disposal of clinicians, insofar as they provide for assessment of biopsies with enhanced objectivity. To this end, various label-free techniques have been developed based on both the inelastic (spectroscopic) and elastic (scattering) interaction between light and tissues. Thus, significant progress has been made in near-infrared spectroscopic imaging of tissues. On the other hand, light scattering methods operate on the assumption that subtle tissue morphological modifications induced by cancer onset and development are accompanied by changes in the scattering properties and, thus, offer a non-invasive window into pathology. Despite these promising efforts, light scattering-based techniques currently have limited use in the clinic. A great challenge is posed by the insufficient knowledge of the tissue optical properties. An ideal measurement will provide the tissue scattering properties over broad spatial scales, which, to our knowledge, remains to be achieved.

SUMMARY OF EMBODIMENTS OF THE INVENTION

In accordance with embodiments of the invention, methods are provided for mapping a characteristic parameter of a specimen, such as a scattering mean free path (MFP) and scattering anisotropy factor based on a quantitative phase shift measurement. The methods have steps of using spatial light interference microscopy (SLIM) to determine a quantitative phase shift as a function of position in a sample, and applying a generalized scatter-phase transformation to derive at least one of a scattering mean free path (MFP), a scattering anisotropy factor, and a thickness-independent parameter as a function of position in the sample. In some cases, the sample may be a slice of tissue.

In an alternate embodiment, both a scattering MFP and a scattering anisotropy factor are derived in a single measurement by application of a generalized scatter-phase transformation.

In accordance with further embodiments of the present invention, methods are provided for detecting calcification in biopsied breast tissue. The methods have steps of using spatial light interference microscopy to determine a quantitative phase shift as a function of position in a slice of the biopsied breast tissue, and detecting calcium phosphate and calcium oxalate based on birefringence relative to surrounding tissue.

In yet further embodiments of the present invention, methods are provided for detecting fibrosis in biopsied prostate tissue. The methods have steps of using spatial light interference microscopy to determine a quantitative phase shift as a function of position in a slice of the biopsied prostate tissue, and detecting fibrosis based on at least one of phase shift variance and scattering mean free path relative to surrounding tissue.

BRIEF DESCRIPTION OF THE DRAWINGS

The present patent or application file contains at least one drawing executed in color. Copies of this patent with color drawing(s) will be provided by the Patent and Trademark Office upon request and payment of necessary fee.

The foregoing features of the invention will be more readily understood by reference to the following detailed description, taken with reference to the accompanying drawings, in which:

FIGS. 4A-4G illustrate the ability of SLIM to reveal particular cell types based on their refractive index signatures, in accordance with embodiments of the present invention.

FIGS. 5A-5D depict a strong refractive index signature of calcium oxylate in breast biopsy tissue, in accordance with embodiments of the present invention, and as further described below.

FIGS. 6A-6J depict images and analyses of tissue of prostate cancer patients, in accordance with embodiments of the present invention, as further described below.

DETAILED DESCRIPTION OF EMBODIMENTS OF THE INVENTION

Definitions

Figure 1A:
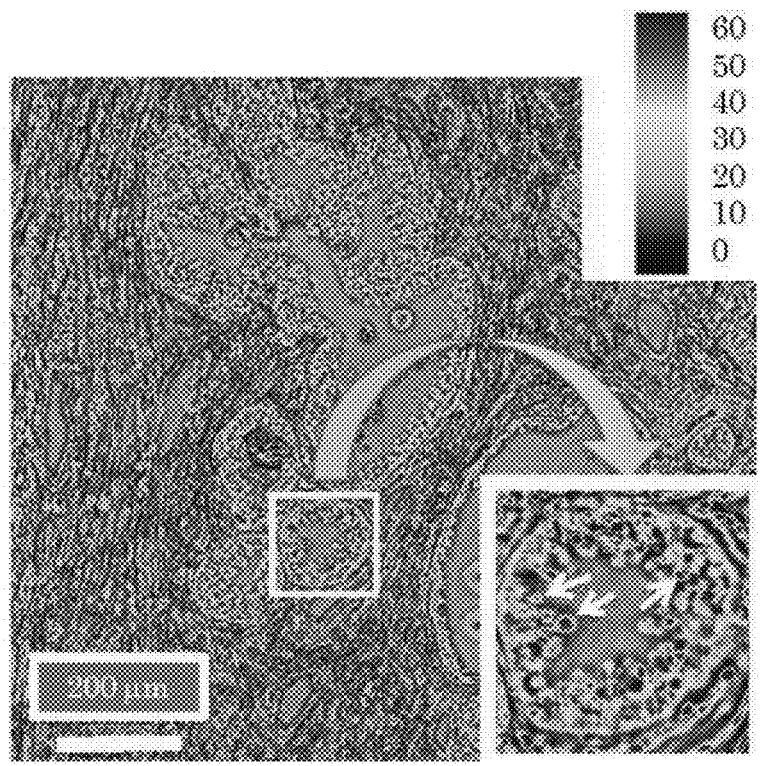
FIG. 1A is an image of a human prostate biopsy obtained using SLIM, while FIG. 1B uses hematoxylin and eosin (H&E) staining. The insets show details of a normal gland and arrows indicate epithelial cells.
Figure 1B:
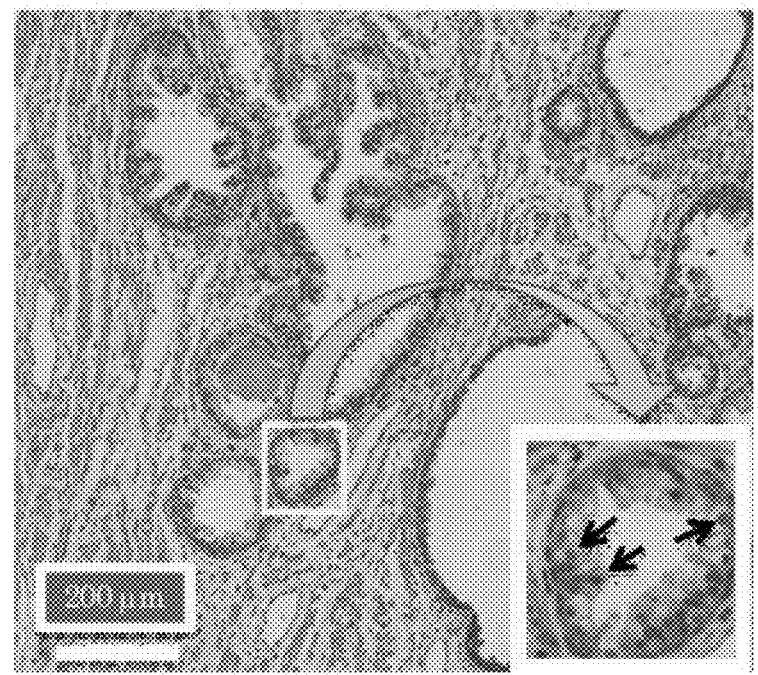
FIGS. 1C and 1D show error estimates for power vs. numerical aperture (NA) and g, and for Δg vs. NA and g, respectively.

As used herein, "label-free" refers to a method of imaging a substantially transparent sample that does not require introduction of materials, such as fluorophores or contrast agents, that are extrinsic to the imaged sample.

The term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereonto. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic or parameter in terms of one or more images.

The terms "object," "sample," and "specimen" shall refer, interchangeably, to a tangible, non-transitory physical object capable of being rendered as an image, and shall encompass, by way of example, tissue (human or otherwise) and cells.

The term "high numerical aperture" shall characterize an optic of numerical aperture (NA) exceeding 0.1, such that approximations based on NA<<1 are inapplicable.

The term "broadband" as applied to a source of irradiation shall refer to a source for which $\Delta k/k_0$ is at least 10%, with $k_0$ denoting the central wavenumber of the spectrum illuminating the sample, while $\Delta k$ denotes the range of illuminating wavenumbers. It is to be understood that, within the scope of the present invention, the wavelength of the source may be swept in time, and that concurrent broadband illumination and post-dispersion detection is employed in preferred embodiments of the invention.

Light-tissue interaction can be modeled by a radiative transport equation, in complete analogy to the problem of neutron transport in reactors. The latter is taught in detail by Duderstadt et al., *Nuclear Reactor Analysis*, (Wiley, 1976), which is incorporated herein by reference. With further simplifying assumptions, a diffusion model can be applied to describe both steady state and time-resolved light transport in tissues. The refractive index of biological structures has been modeled both as discrete particle distribution and as a continuous or fractal distribution, described by Hunter, et al., *Phys. Rev. Lett.*, vol. 97, 138102 (2006), which is incorporated herein by reference.

In accordance with embodiments of the present invention, quantitative phase imaging of thin slices of tissue is used to spatially map the tissue in terms of its scattering properties. More specifically, mathematical relationships are established between the phase map $\phi(x, y)$ associated with a tissue slice of thickness L<<$l_s$, (see FIG. 1) and scattering parameters of the bulk, such as $l_s$ and g, the scattering mean free path, and the anisotropy factor, respectively.

As a preliminary matter, it was shown in Wang et al., *Scattering-phase theorem*, Opt. Lett., vol. 36, pp. 1215-16 (Apr. 1, 2011) (hereinafter, Wang (2011A), incorporated herein by reference) that the scattering mean free path $l_s$ averaged over a certain area across a tissue slice is directly related to the mean-squared phase (variance of the phase) within that region. It was also proven, in Wang (2011A), that the anisotropy factor g relates to the phase gradient distribution. These relations, which are referred to collectively to as the "scattering-phase theorem," are expressed as $$l_s = \frac{L}{\langle \Delta\phi^2(r) \rangle_r}, \quad \text{(Eqn. 1a)}$$

$$g = 1 - \left(\frac{l_s}{L}\right)^2 \frac{\langle |\nabla[\phi(r)]|^2 \rangle_r}{2k_0^2}. \quad \text{(Eqn. 1b)}$$

In Eqns. 1a and 1b,
L is the tissue slice thickness, L<<$l_s$;
$\langle \Delta\phi^2(r) \rangle_r = \langle [\phi(r) - \langle \phi(r) \rangle_r]^2 \rangle$ is the phase variance, with $\langle \rangle_r$ denoting spatial average over a certain area;
$k_0 = 2\pi/\lambda$, with $\lambda$ the mean wavelength of light in tissue; and $|\nabla[\phi(r)]|^2 = (\partial\phi/\partial x)^2 + (\partial\phi/\partial y)^2$ is the modulus squared of the phase gradient, with r=y). Here the definition of g is extended to continuous distributions of refractive index: it is the average cosine of the scattering angle associated with a slice of thickness $l_s$. This way, the assumption that the tissue is made of discrete particles is removed.

DEFINITION

As used herein, and in any appended claim, the term "scatter phase transformation" shall refer to any transformation of variables applying the scatter-phase theorem expressed in Eqns. 1A and 1B. The term "generalized scatter phase transformation" shall encompass Eqns. 1A and 1B and any transformation corresponding to higher-order statistical moments, such as skewness, kurtosis, etc.

In accordance with one embodiment of the present invention, spatial light interference microscopy (SLIM) may be used, although it is to be understood that the invention described herein is not limited to the use of SLIM to obtain quantitative phase imaging (QPI), and that other methods of QPI, now known, or discovered in the future, are within the scope of the present invention.

SLIM is a quantitative phase imaging method described in U.S. Pat. No. 8,184,298, and in Wang et al., *Spatial Light Interference Microscopy, Opt. Exp.*, vol. 19, pp. 1016-26 (2011) (hereinafter, Wang 2011B, incorporated herein by reference). SLIM, which may use broadband light centered at 535 nm, provides highly sensitive quantitative phase images, typically with 0.03 nm path-length sensitivity temporally, and 0.3 nm spatially.

Example I

In an example of the application of the present invention, two adjacent 4 μm-thick tissue biopsies, one unstained and one stained by hematoxylin and eosin stain (H&E) were imaged by SLIM and in a bright field microscope, respectively. FIGS. 1A-1D illustrate the ability of SLIM to render high transverse resolution, high phase sensitivity images of thin tissue slices. The phase information provided by SLIM is inherently averaged over the optical frequencies, as discussed by Wang, et al., *Appl. Phys. Lett.*, vol. 96, 051117 (2010), which is incorporated herein by reference. Thus, the scattering parameters obtained by this method will also be frequency-averaged. Throughout the experiments discussed here in the context of the present application, a 10×, 0.3 NA objective was used. This limited numerical aperture effectively acts as a low-pass spatial frequency filter.

The spatial averages performed in deriving equations 1a-b are expected to be affected by this cut-off of the limited numerical aperture. Because tissues scatter strongly forward (g close to 1), it is anticipated that the low NA is not a significant error source. However, in order to quantify this effect, the common Henyey-Greenstein angular distribution was used to calculate the respective error functions, $$\Delta P(NA, g) = 1 - \int_{\sqrt{1-NA^2}}^{1} P(\cos\theta) \, d\cos\theta \quad \text{(Eqn. 2a)}$$

$$\Delta g(NA, g) = 1 - \int_{\sqrt{1-NA^2}}^{1} \cos\theta P(\cos\theta) \, d\cos\theta \quad \text{(Eqn. 2b)}$$

where P is the Henyey-Greenstein distribution, normalized to unit area, $$P(\cos\theta) \propto (1-g^2)/(1+g^2-2g\cos\theta)^{3/2}.$$

Figure 1C:
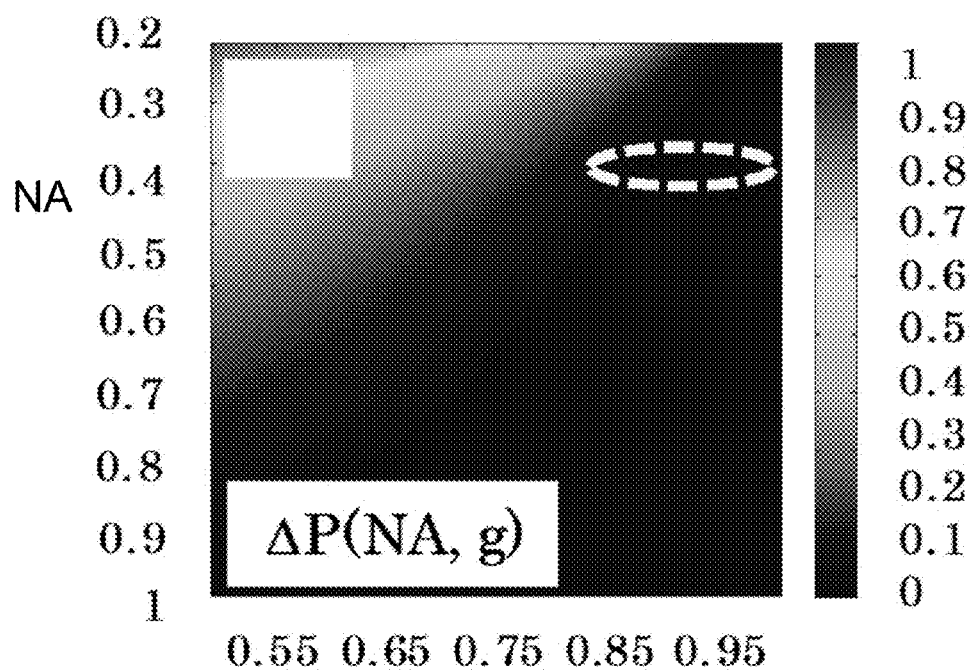
Figure 1D:
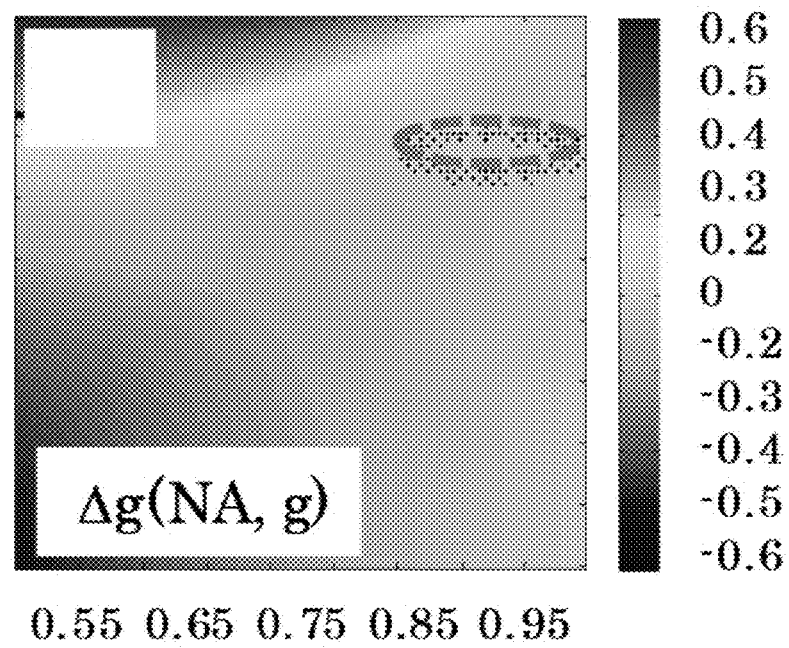

In Eqns. 2a-b, $\Delta P$ represents the scattered power that is not accounted for due to NA, and $\Delta g$ represents the difference between the measured and true average cosine of the scattering angle (i.e., g). FIGS. 1C-1D show the two error functions, $\Delta P$ and $\Delta g$ in a space of NA and g. It can be seen that, in the measurement range set by the NA=0.3 employed, and by the large g values associated with tissues (ellipses in FIGS. 1C-1D), the errors are below 10% in power and 5% in g, and decrease accordingly for higher NA.

A systematic error in the thickness of the tissue slice will introduce errors in the $l_s$ and g values. The tissue biopsies used in the study of Example I were sectioned using high-precision microtome at 5 μm thickness, with <1 μm accuracy. This error of maximum 20% in the measured $l_s$ is higher than that provided by the instrument in terms of phase imaging. However, in all applications of medical relevance, the ratio in values for normal and diseased tissues rather than their absolute value is of interest. Measuring this ratio is thickness-independent and, thus, subject to much better accuracy. Thickness-independent variables such as mean²/variance have diagnostic value, as discussed in detail in Wang, *Tissue refractive index as marker for disease*, *Journal of Biomedical Optics*, vol. 16, 116017 (Nov. 4, 2011), which is incorporated herein by reference.

Example II

Figures 2A, 2B, 2C:
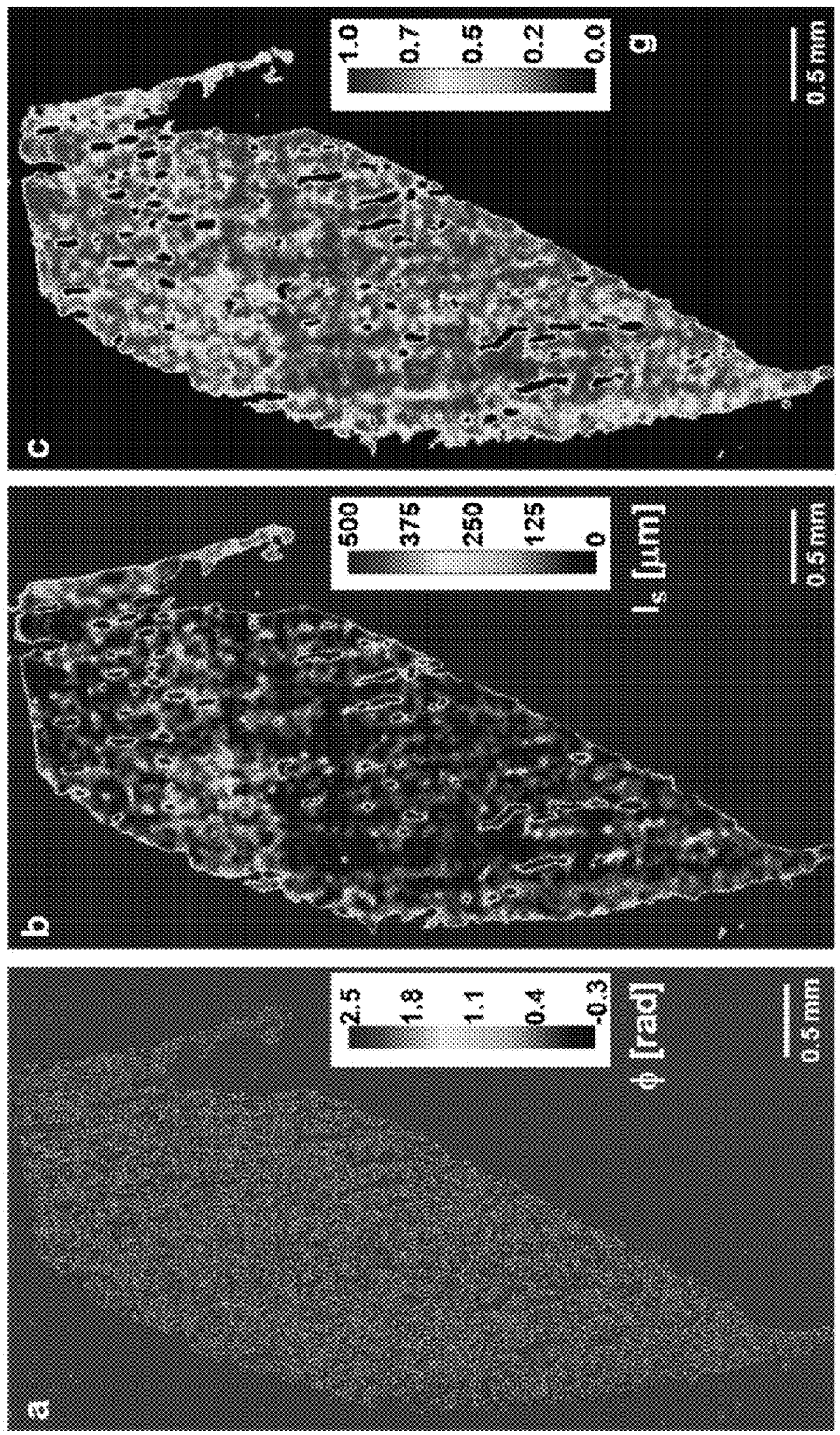
FIG. 2A shows a quantitative phase image of a tissue slice cut from a three month old rat liver.
FIGS. 2B and 2C show maps of $l_s$ and g for the same rat liver as shown in FIG. 2A, in accordance with embodiments of the present invention.

In a further example of the application of the present invention, quantitative phase images associated with 5-1 μm thick tissue slices from rat organs were acquired. The tissue was sliced frozen but thawed before imaging. Three slices from each organ of the same rat were cut in succession and imaged by SLIM. The field of view of the microscope was 0.4×0.3 mm². In order to image the cross-section of the entire organ, the specimen was translated and a mosaic of quantitative phase images was acquired and numerically collaged together. Single quantitative phase images made of hundreds of individual SLIM images were obtained. Note that these quantitative phase images cover the entire cross section of a rat organ, with a resolution of ~λ/2NA=0.9 μm. FIG. 2A shows one example of quantitative phase image of a tissue slice cut from a three month old rat liver.

Following Eq. 1, $l_s$ and g were calculated in windows of 9×9 μm² across the entire tissue slice. FIGS. 2B and 2C show maps of $l_s$ and g for the same rat liver as shown in FIG. 2A. As exemplified in FIGS. 2B and 2C, an image may be displayed, in accordance with embodiments of the present invention, mapping one or more characteristic parameters as a function of position in a sample.

Figure 3A:
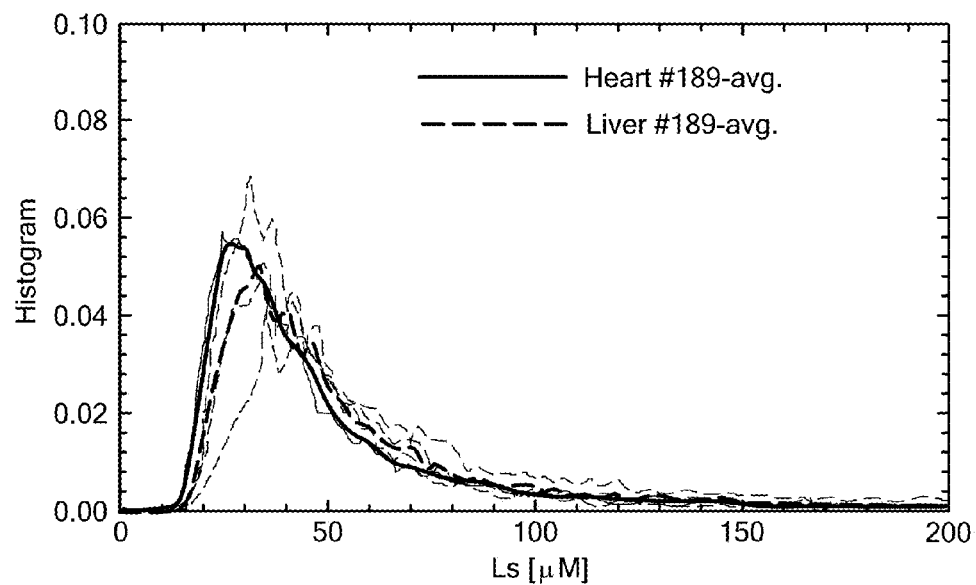
FIGS. 3A-3B show histograms of $l_s$ and g obtained from rat liver and heart sections.
Figure 3B:
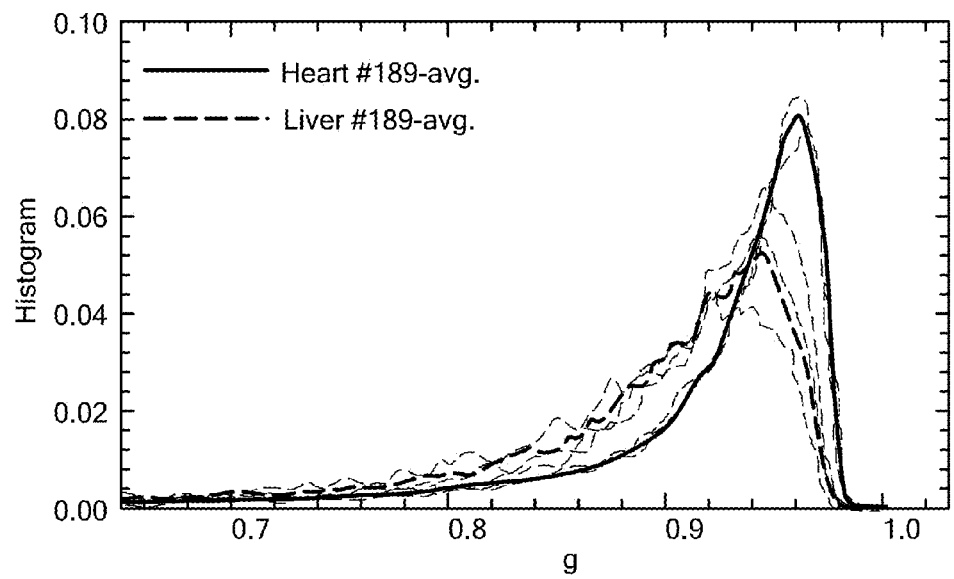

Results obtained for rat liver are compatible with values obtained by diffusion scattering measurements described in Ding (2009). It is apparent that the tissue scattering parameters exhibit strong inhomogeneities across the organ, mainly due to inclusions which induce refractive index fluctuations. Note that the background $l_s$ values are very high, indicating lack of scattering, as expected. The histogram of $l_s$ and g obtained from rat liver and heart sections are presented in FIGS. 3A-B. The average $l_s$ was found to be smaller for heart than for liver, which indicates that the unscattered light decays faster in the heart. Furthermore the anisotropy factor is higher for heart, which is associated with a more dominant forward scattering.

Figure 3C:
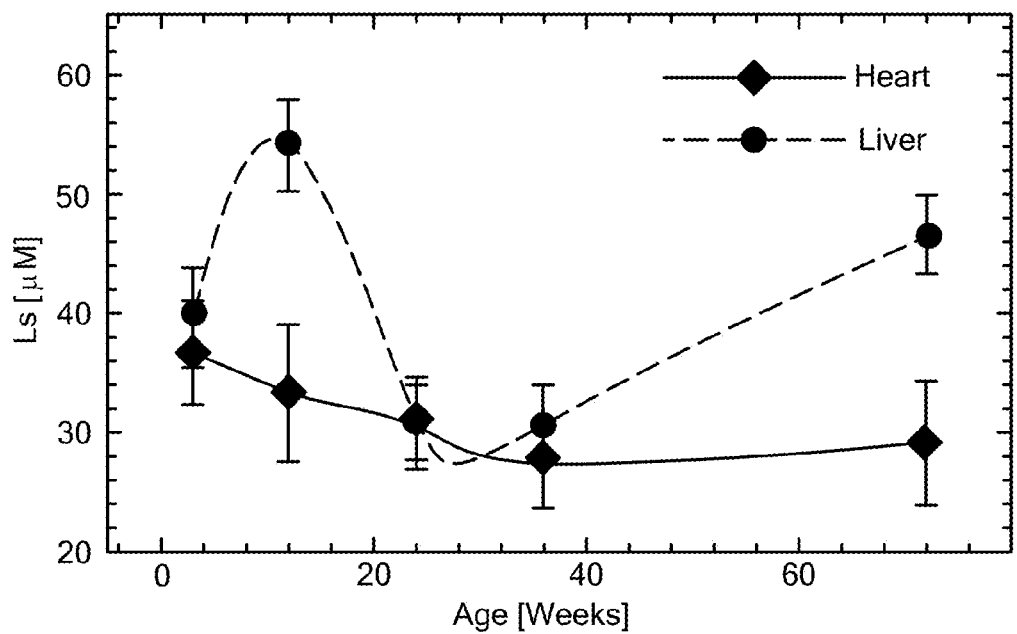
FIGS. 3C-3D map scattering parameters as a function of rat age.
Figure 3D:
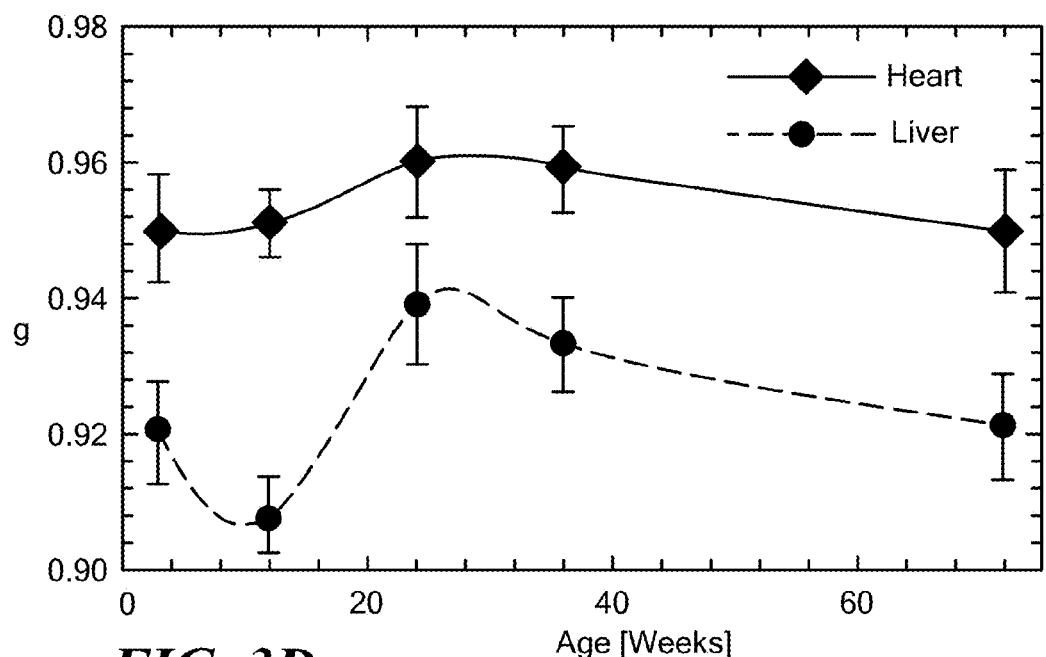

Nevertheless, the measurements performed uniquely underline the significant spread in the measured values for both parameters, which is an important aspect when aiming for diagnosis. The procedure described was used to map rat organs at five different ages: 3 weeks, 3 months, 6 months, 9 months and 18 months. The results are summarized in FIGS. 3c-d in terms of the modes of the distributions. While variations of these modes with age are apparent, these changes are within the widths of the distributions. The only conclusions that can be drawn are probabilistic, for example, the most probable $l_s$ value decreases slightly with age in heart tissues. The most probable g values seem to remain roughly constant in time, but distinct for the two both organs. The apparent correlations between $l_s$ and g, especially for liver, may suggest that both $l_s$ and g track the morphology of the tissue with age, but it is difficult to draw a conclusion based on this limited data set.

As shown in the foregoing examples, fast and spatially resolved access to tissue scattering mean free path $l_s$ and anisotropy factor g may be advantageously obtained from quantitative phase images of thin tissue slices. SLIM provides nanoscale information about the tissue structure, which in itself sets the basis for a new type of label-free diagnosis of biopsies. The knowledge of $l_s$ and g has great impact on predicting the outcome of a broad range of scattering experiments on large samples.

In accordance with other embodiments of the present invention, quantitative phase imaging (QPI) is employed, particularly, for label-free pathology. In cases where tissue thickness is known, SLIM may be employed to obtain quantitative images of phase, thereby capturing spatial fluctuations of the refractive index. This information fully determines the light-tissue elastic interaction, i.e., its light scattering properties, as discussed in Wang (2011A). The refractive index is proportional to the tissue dry mass concentration, which provides complementary information with respect to the dye affinity revealed in common histopathology.

Example III

Refractive Index Signatures at the Cellular Scale

Figure 4G:
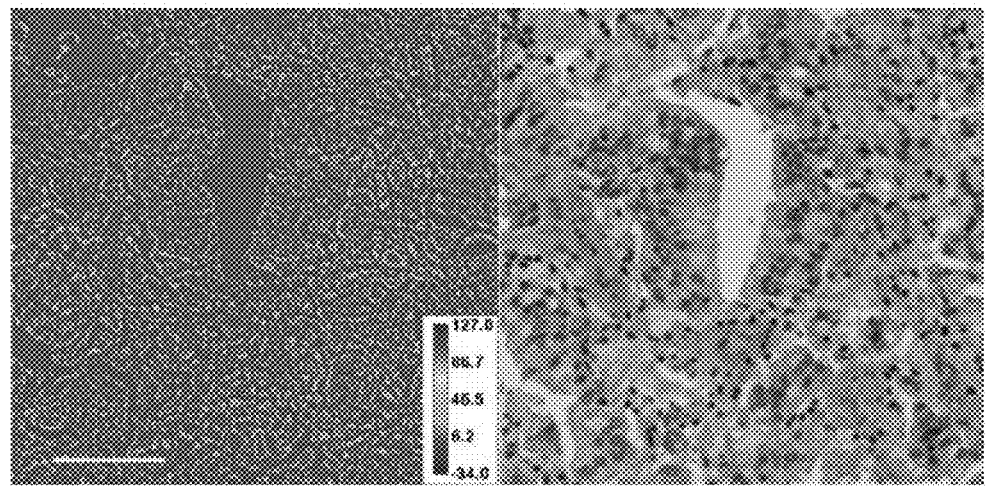
Figure 4G:
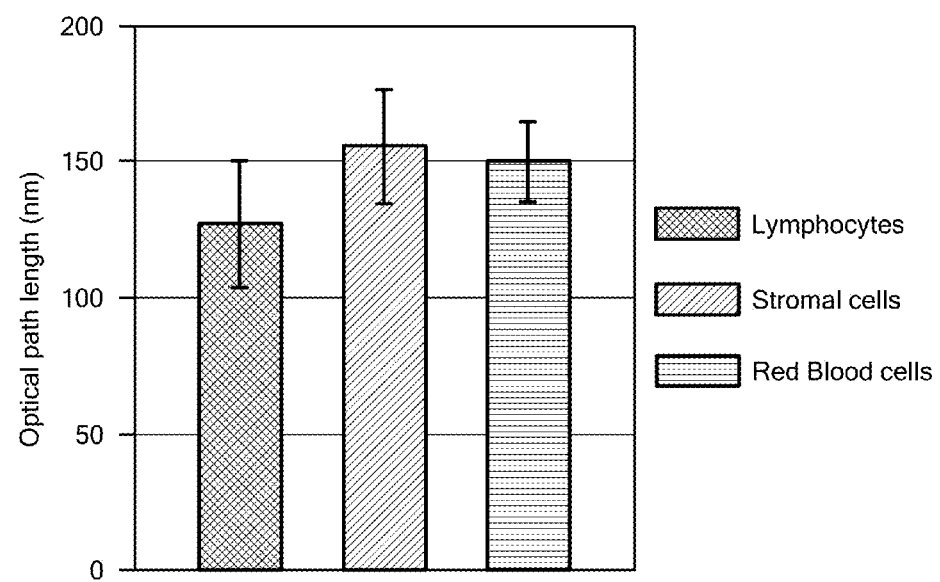

Both SLIM and stained tissue images were obtained using a 10× (NA=0.3) objective, which captures multiscale information down to subcellular structures. FIGS. 4A-4G illustrate the ability of SLIM to reveal particular cell types based on their refractive index signatures. Due to their discoid shape and high refractive index, red blood cells are easily identifiable in the SLIM images (FIGS. 4A-4B). Lymphocytes, as evidenced by dark staining in H&E (FIG. 4D), were found to exhibit high refractive index in SLIM images (FIG. 4C). The lymphocytes were confirmed by utilizing immunohistochemical stain, namely Leuckocyte Common Antigen (CD45) (FIG. 4E). In a different area of the tissue, a particular type of cell was that seems unlike the rest: while their refractive index is distinctly high, they are sparsely distributed within the tissue (FIG. 4F). In H&E, they appear as black dots. Due to their negative immunostaining for epithelial, myoepithelial, and lymphocytes, these particular cells were identified as stromal.

A semi-automatic segmentation program based on ImageJ (available for download from the National Institutes of Health) was also used to analyze the maximal phase value for the three different type of cells. 326 red blood cells, 278 lymphocytes and 201 stromal cells were identified and analyzed (FIG. 2G). The t-tests of the data show that the significance value (p value) for lymphocyte vs. red blood cell and lymphocyte vs. stromal cell is essentially zero ($3.37\ e^{-38}$ and $4.50\ e^{-38}$, respectively), while for stromal vs. red blood cell, $p=6.43\ e^{-4}$, indicating that the three cell types have their refractive index statistically different. While encouraging, the t-tests results hold little relevance for a small number of cells, when distinguishing among these high-refractive index cells becomes challenging. However, it is possible to take the advantage of the spatial relations, i.e. refractive index correlations, to sort these cells within the biopsy. Note that other cells, e.g., epithelial cells and myoepithelial cells (FIG. 4A), relevant for diagnosing prostate cancer, have much lower phases and, thus, can be distinguished quite easily. Therefore, SLIM reveals intrinsic optical properties of cellular and subcellular structures in unstained tissue biopsies. This capability is exploited below in problems of clinical relevance: breast and prostate tissue diagnosis.

Example IV

Detection of Micro-Calcifications in Breast Biopsies

Further, we found interesting optical maps associated with calcifications in the breast. Mammography is an important screening tool for detecting breast cancer. Presence of abnormal calcifications, i.e. calcium phosphate and calcium oxalate, warrants further work up. Distinguishing between calcium oxalate and calcium phosphate is clinically important. Specifically, it is uncommon for calcium oxalate crystals to be associated with breast malignancy, though it can be associated with papillary intraductal carcinoma. Calcium oxalate crystals account for 12% of mammographically localized calcifications that typically prompt for a biopsy procedure. Calcium oxalate is more difficult to detect radiologically and these crystals are easily missed in the biopsies because they do not stain with H&E. These crystals are birefringent and, thus, can be observed in polarized light. However, if the index of suspicion is not high, the pathologist typically does not use polarization microscopy and calcium oxalate can be missed. The apparent absence of calcification in tissue biopsies reported by the pathologist has significant clinical impact, including repeated mammograms and additional, unnecessary surgical intervention. Therefore, a consistent means for detecting calcium oxalate is desirable as it decreases significantly medical costs and patient anxiety.

FIG. 5 illustrates how SLIM may fulfill this challenging task. In FIG. 5B, the dark H&E staining was identified by pathologists as calcium phosphate. This structure is revealed in the SLIM image as having inhomogeneous refractive index, with a different texture from the surrounding tissue. More importantly, the calcium oxalate crystals are hardly visible in H&E (FIG. 5D); the faint color hues are due to the birefringence of this type of crystal. Clearly, calcium oxalate exhibits a strong refractive index signature, as evidenced by the SLIM image (FIG. 5C). In accordance with certain embodiments of the invention, spatial light interference microscopy may be employed to determine a quantitative phase shift for distinct polarizations as a function of position in a slice of the biopsied breast tissue in order to identify a birefringence characteristic of calcium phosphate and calcium oxalate relative to surrounding tissue.

Example V

Refractive Index as Marker for Prostate Cancer

Figure 6F:
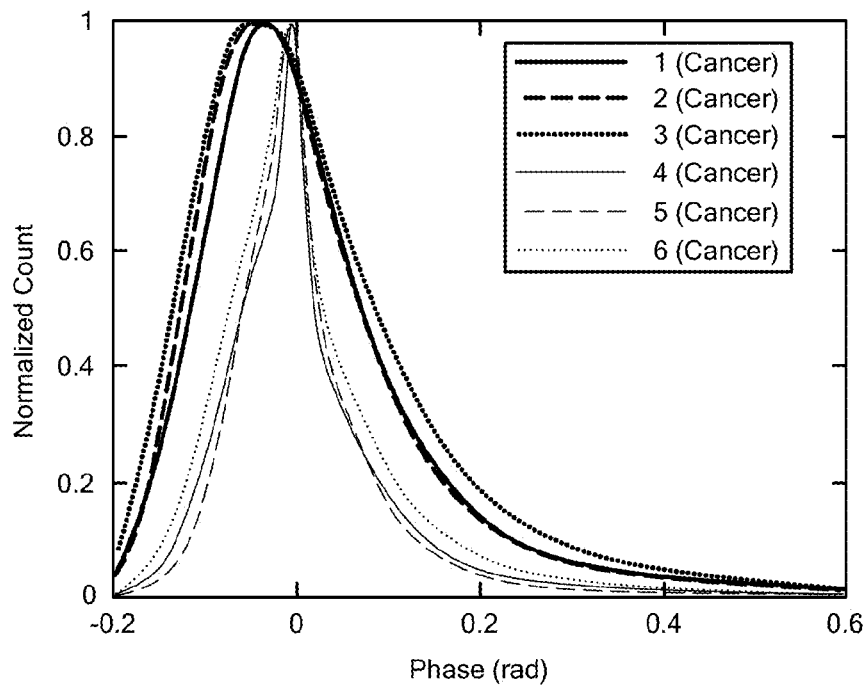
Figure 6G:
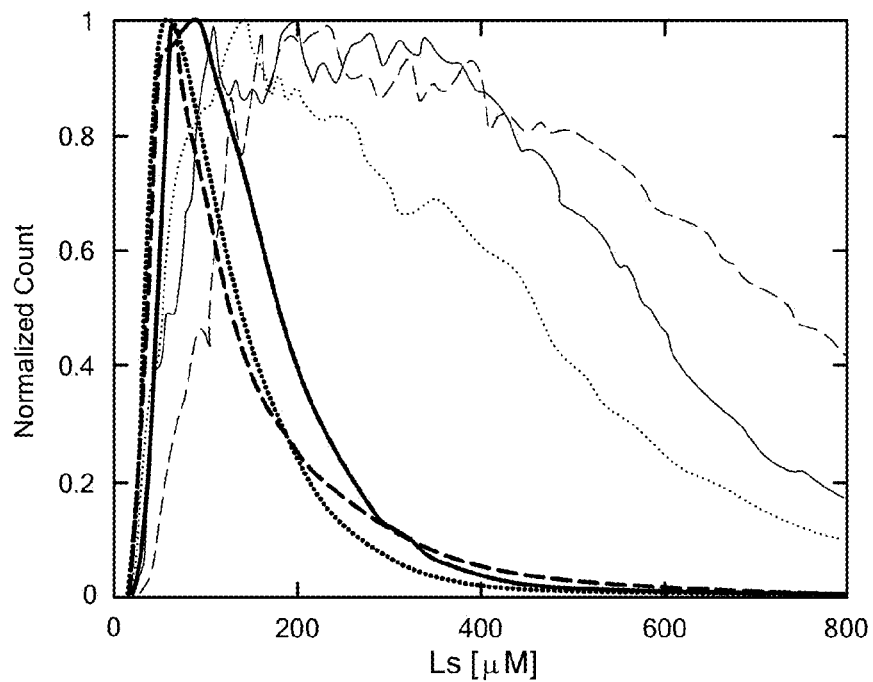
Figure 6H:
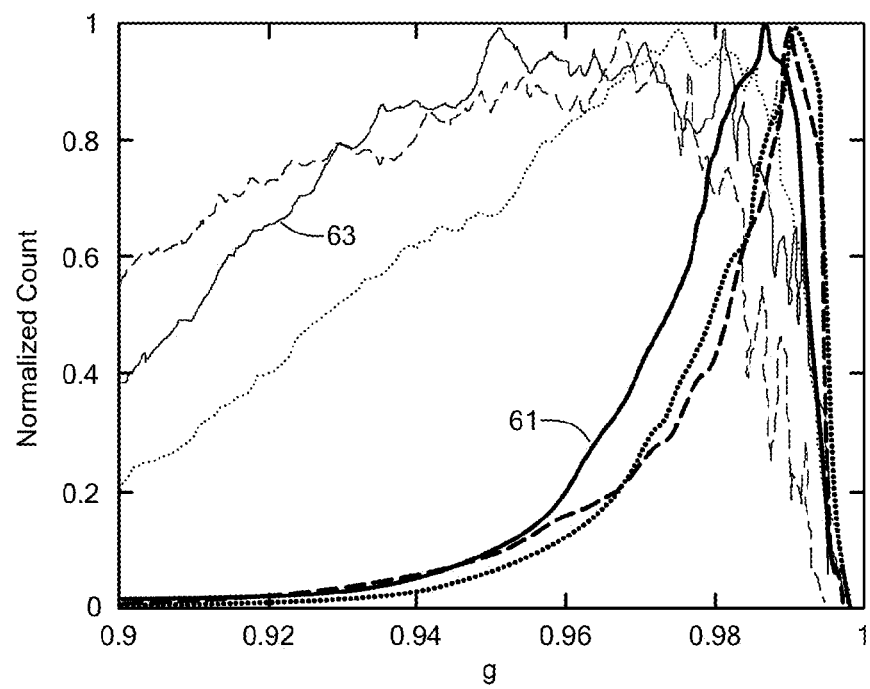
Figure 6I:
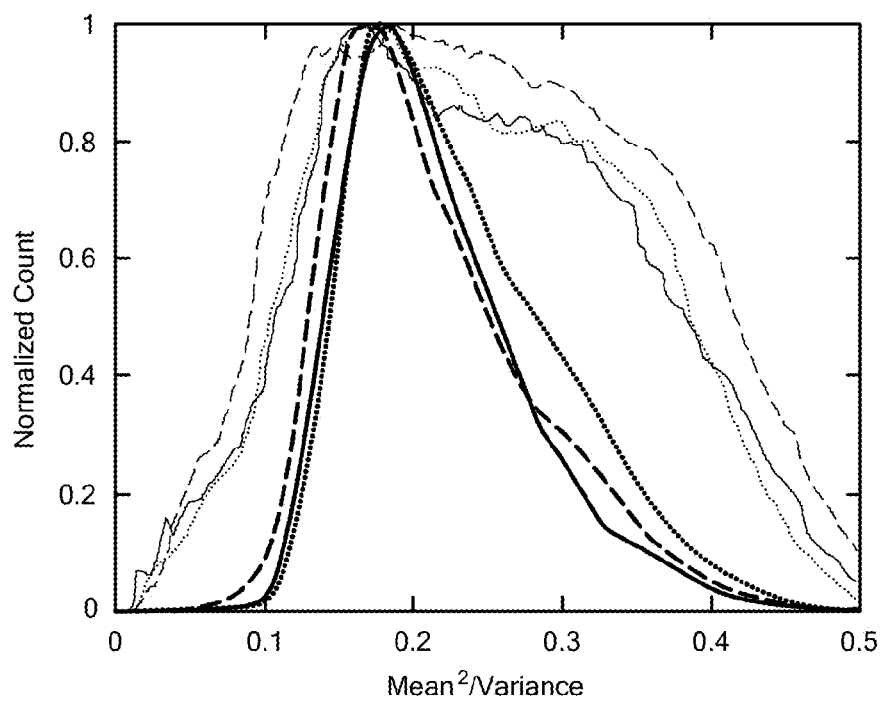

In a further example of application of methods in accordance with embodiments of the present invention, biopsies from prostate cancer patients were studied. Eleven biopsies from 9 patients were imaged with both SLIM and H&E, as illustrated in FIGS. 6A and 6E, respectively. For each biopsy, the pathologist identified regions of normal and malignant tissue. From the SLIM image, the map of phase shift variance, $\langle \Delta\phi(r)^2 \rangle$, was computed, where the angular brackets denote spatial average (calculated over $32\times32\ \mu m^2$) and $r=(x,\ y)$. FIG. 4B illustrates the map of the scattering mean free path, calculated from the variance as $l_s=L/\langle \Delta\phi(r)^2 \rangle$, as described above. The spatially resolved scattering map shows very good correlation with cancerous and benign areas. It can be easily seen that the regions of high variance, or short scattering mean free path, correspond to the darker staining in H&E, which is associated with the tumor. These findings confirm in a direct way the importance of tissue light scattering as means for cancer diagnosis. Essentially, the measurements described here and performed in accordance with embodiments of the present invention indicate that prostate cancer renders the tissue more inhomogeneous, which makes it more strongly scattering. These findings are further confirmed by the anisotropy factor measurements (FIG. 6C), where malignant areas exhibit consistently higher values of g. These data indicate that cancer affects the tissue architecture in such a way as to render it more inhomogeneous (lower $l_s$), characterised by angular scattering that is more biased toward the forward direction (higher g). Of course, the absolute values for $l_s$ and g are sensitive to the thickness of the tissue. However, because the refractive index contrast is usually very small, the optical thickness is also very small. Furthermore, cutting errors, if present, are expected to occur at much larger scales than our window used for computation (32×32 µm²). We seldom observe uneven phase distributions within the same slides covering very large areas of cm². Within each slice, the scattering parameter map allows for cancer detection, in which ratios (normal vs. cancer) rather than absolute values are of interest. Still, it is possible to introduce some parameters that are independent of the section thickness. One example is the mean squared of the phase divided by the variance (FIGS. 6D and 6I). This quantity indicates the "contrast" of the refractive index fluctuations.

Figure 6J:
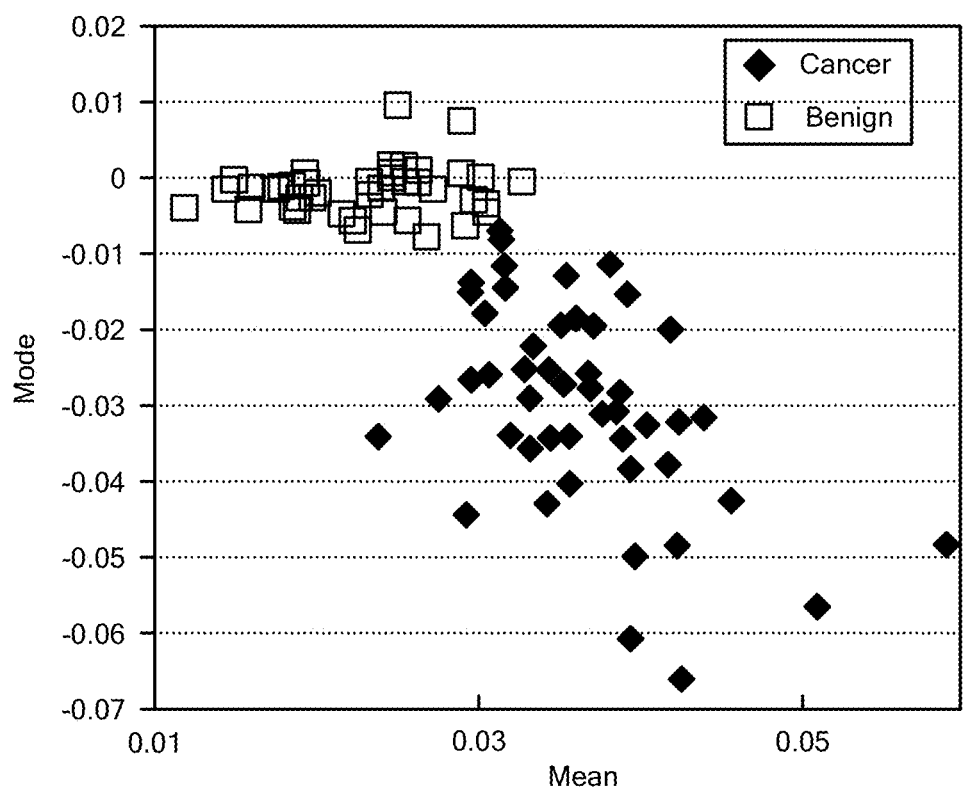

In order to quantitatively analyze the information contained in the refractive index distribution for the tumor and benign regions, we computed statistical parameters of the $1^{st}$ to $4^{th}$ order via the respective histograms. FIGS. 6F-6I show the histograms associated with regions in the maps of FIG. 6A-6D, respectively. Based on these distributions, the mean, standard deviation, mode, skewness, and kurtosis for each of the 49 cancer and 51 benign areas were calculated. Unambiguous tumor 61 and normal 63 regions were selected by a Board Certified pathologist using the H&E slides. The pathologist did not have access to phase images prior to this selection. A second certified pathologist confirmed the classification of the regions in terms of normal vs. tumor. Many different parameters and statistics were processed before arriving at the representation of highest separation. Out of the eleven biopsies, seven were diagnosed by the Board Certified pathologist as Gleason grade 6/10, two cases Gleason grade 7/10, one case Gleason grade 9/10, and one case was benign. With this numerical processing, a multi-dimensional data space was generated in which a search was conducted for the most confident separation between the two groups of data points. Clearly, the mode vs. mean (FIG. 6J) separates the normal from the diseased areas completely from the data set of 100 regions total.

In preferred embodiments of the present invention, the disclosed methods for quantitative phase imaging of transparent structures and for derivation of scattering parameters are implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for mapping a characteristic parameter of a specimen in a single measurement, the method comprising:
   a. using spatial light interference microscopy to determine a quantitative phase shift as a function of position in a sample;
   b. applying a generalized scatter-phase transformation to derive at least one of a scattering MFP, a scattering anisotropy factor, and a thickness-independent parameter, as a function of position in the sample; and
   c. displaying an image of the characteristic parameter as a function of position in the sample.

2. A method in accordance with claim 1, wherein the characteristic parameter is a thickness-independent parameter equal to a ratio of a variance of the quantitative phase shift to a square of a mean of the quantitative phase shift.

3. A method in accordance with claim 1, wherein the sample includes a slice of tissue.

4. A method in accordance with claim 1, further comprising determining the scattering MFP and the scattering anisotropy factor in a single measurement.

5. A method in accordance with claim 1, wherein the sample includes biopsied breast tissue, and wherein the step of using spatial light interference microscopy to determine a quantitative phase shift as a function of position in a sample includes determining a quantitative phase shift for distinct polarizations as a function of position in a slice of the biopsied breast tissue,
   the method further comprising:
   d. detecting calcium phosphate and calcium oxalate based on birefringence relative to surrounding tissue.

6. A method in accordance with claim 1, wherein the sample includes biopsied prostate tissue,
   the method further comprising:
   d. detecting fibrosis based on at least one of phase shift variance and scattering mean free path relative to surrounding tissue.

* * * * *